US011786480B2

(12) United States Patent
Hamada et al.

(10) Patent No.: US 11,786,480 B2
(45) Date of Patent: Oct. 17, 2023

(54) TRANSDERMALLY ABSORBABLE PREPARATION

(71) Applicant: KM TRANSDERM LTD., Osaka (JP)

(72) Inventors: Atsuyo Hamada, Higashikagawa (JP); Masaoki Goto, Higashikagawa (JP)

(73) Assignee: KM TRANSDERM LTD., Osaka (JP)

( * ) Notice: Subject to any disclaimer, the term of this patent is extended or adjusted under 35 U.S.C. 154(b) by 0 days.

(21) Appl. No.: 16/060,642

(22) PCT Filed: Dec. 9, 2016

(86) PCT No.: PCT/JP2016/086819
§ 371 (c)(1),
(2) Date: Jun. 8, 2018

(87) PCT Pub. No.: WO2017/099246
PCT Pub. Date: Jun. 15, 2017

(65) Prior Publication Data
US 2019/0000774 A1    Jan. 3, 2019

(30) Foreign Application Priority Data
Dec. 10, 2015  (JP) ................. 2015-257760

(51) Int. Cl.
| A61K 9/70 | (2006.01) |
| A61K 31/445 | (2006.01) |
| A61K 47/06 | (2006.01) |
| A61K 47/12 | (2006.01) |
| A61K 47/14 | (2017.01) |
| A61K 47/32 | (2006.01) |

(52) U.S. Cl.
CPC .............. *A61K 9/7053* (2013.01); *A61K 9/70* (2013.01); *A61K 31/445* (2013.01); *A61K 47/06* (2013.01); *A61K 47/12* (2013.01); *A61K 47/14* (2013.01); *A61K 47/32* (2013.01)

(58) Field of Classification Search
None
See application file for complete search history.

(56) References Cited

U.S. PATENT DOCUMENTS

| 2004/0258741 | A1 | 12/2004 | Terahara et al. | |
| 2007/0104773 | A1* | 5/2007 | So | A61K 8/0208 424/449 |
| 2010/0260826 | A1 | 10/2010 | Makabe et al. | |
| 2011/0056863 | A1 | 3/2011 | Sekiya et al. | |
| 2011/0243998 | A1 | 10/2011 | Sakamoto et al. | |
| 2012/0323190 | A1* | 12/2012 | Ito | A61K 31/13 604/307 |
| 2013/0226112 | A1 | 8/2013 | Akazawa et al. | |
| 2014/0308335 | A1* | 10/2014 | Hamada | A61K 31/445 424/443 |
| 2015/0250877 | A1* | 9/2015 | Umemoto | A61K 9/7061 424/449 |
| 2015/0374642 | A1 | 12/2015 | Ogino et al. | |
| 2016/0206568 | A1 | 7/2016 | Ogino et al. | |
| 2017/0333367 | A1 | 11/2017 | Ogino et al. | |
| 2017/0367994 | A1 | 12/2017 | Hamada et al. | |

FOREIGN PATENT DOCUMENTS

| CN | 1571664 A | 1/2005 |
| CN | 102014905 A | 4/2011 |
| CN | 102204897 A | 10/2011 |
| CN | 102188363 A | 11/2011 |
| EP | 0947193 A2 | 10/1999 |
| EP | 1437130 A1 | 7/2004 |
| EP | 1985290 A1 | 10/2008 |
| EP | 2279739 A1 | 2/2011 |
| JP | H07-126157 A | 5/1995 |
| JP | H07-145047 A | 6/1995 |
| JP | H07-215850 A | 8/1995 |
| JP | H09-291028 A | 11/1997 |
| JP | H09-301854 A | 11/1997 |
| JP | H10-179711 A | 7/1998 |
| JP | H10-316559 A | 12/1998 |
| JP | H11-130626 A | 5/1999 |
| JP | H11-315016 A | 11/1999 |
| JP | 2001-302502 A | 10/2001 |
| JP | 2002-212064 A | 7/2002 |
| JP | 2006-206454 A | 8/2006 |
| JP | 2007-119405 A | 5/2007 |
| JP | 2010-248076 A | 11/2010 |
| JP | 2011-020997 A | 2/2011 |
| JP | 2011-225536 A | 11/2011 |

(Continued)

OTHER PUBLICATIONS

European Patent Office, Extended European Search Report in European Patent Application No. 16873139.6 (dated Jul. 16, 2019).
Japanese Patnet Office, International Search Report in International Patent Application No. PCT/JP2016/086819 (dated Jan. 31, 2017).
China National Intellectual Property Adminstration, The First Office Action in Chinese Patent Application No. 201680081472.1 (dated Jun. 1, 2020).
Japanese Patent Office, Notice of Reasons for Refusal in Japanese Patent Application No. 2021-089233 (dated Mar. 29, 2022).
Japan Patent Office, Notice of Reasons for Refusal in Japanese Patent Application No. 2021-089233 (dated Nov. 22, 2022).
Japan Patent Office, Decision of Refusal in Japanese Patent Application No. 2021-089233 (dated May 5, 2023).
Japan Patent Office, Decision of Dismissal of Amendment in Japanese Patent Application No. 2021-089233 (dated May 5, 2023).

*Primary Examiner* — Brian Gulledge
(74) *Attorney, Agent, or Firm* — Leydig, Voit & Mayer, Ltd.

(57) ABSTRACT

The present invention provides a transdermal absorption preparation in which a drug-containing adhesive layer is formed on a support, the aforementioned adhesive layer contains at least a thermoplastic elastomer and a higher fatty acid ester, and a content of a tackifier is not more than 10 wt %, which is superior in drug solubility and releasability, as well as adhesiveness to the skin and low irritation to the skin.

9 Claims, 3 Drawing Sheets

(56) References Cited

FOREIGN PATENT DOCUMENTS

| | | |
|---|---|---|
| JP | 2012-149061 A | 8/2012 |
| JP | 2015-113339 A | 6/2015 |
| WO | 2003/032960 A1 | 4/2003 |
| WO | 2012/029325 A1 | 3/2012 |
| WO | 2013/035850 A1 | 3/2013 |
| WO | WO-2013035850 A1 * 3/2013 ........... A61K 31/445 |
| WO | 2014/051128 A1 | 4/2014 |
| WO | WO 2014/200072 A1 | 12/2014 |
| WO | WO-2015111862 A1 * 7/2015 .............. A61P 25/28 |
| WO | 2016/088898 A1 | 6/2016 |

* cited by examiner

TRANSDERMALLY ABSORBABLE PREPARATION

CROSS-REFERENCE TO RELATED APPLICATIONS

This patent application is the U.S. national phase of International Patent Application No. PCT/JP2016/086819, filed Dec. 9, 2016, which claims the benefit of Japanese Patent Application No. 2015-257760, filed on Dec. 10, 2015, which are incorporated by reference in their entireties herein.

TECHNICAL FIELD

The present invention relates to a transdermal absorption preparation having sufficient drug solubility, transdermal permeability, and sufficient adhesiveness to the skin and showing low skin irritation.

BACKGROUND ART

When a drug is to be transdermally absorbed, the drug is added to an adhesive base and the like and formed as a transdermal absorption preparation. In recent years, tapes more superior in the adhesiveness are often used than poultices containing a large amount of water as a constituent component in a transdermal absorption preparation. As an adhesive base for such tapes, a lipophilic adhesive base such as of rubber, acrylic or silicone type and the like is used. Of these, a rubber adhesive base is widely used since additives can be easily blended as compared to other adhesive bases (patent documents 1-3).

However, problems have been pointed out even for a transdermal absorption preparation using a rubber adhesive base such as uninsurable sufficient releasability of a drug, development of skin irritation caused by a tackifier generally added to a transdermal absorption preparation and the like.

Under such circumstances, the present inventors have found that an adhesive sheet for adhesion to the skin, which has sufficient adhesiveness and shows low skin irritation, can be obtained even without using a tackifier but by using a thermoplastic elastomer and a large amount of liquid paraffin relative to the elastomer, and that a transdermal absorption preparation having sufficient transdermal absorbability can be obtained by adding a drug or a pharmaceutically acceptable salt thereof to the adhesive sheet (patent document 4).

However, depending on the drug to be contained and in some cases, the solubility of the drug in the base is insufficient, crystals are precipitated or sufficient skin permeability cannot be achieved.

On the other hand, donepezil (i.e., 1-benzyl-4-(5,6-dimethoxyindanon-2-yl)methylpiperidine) is widely used for the treatment of mild to moderate levels of Alzheimer-type dementia, generally in the form of hydrochloride (i.e., donepezil hydrochloride). Alzheimer-type dementia is a disease wherein the normal function of the brain is gradually lost since the nerve cells constituting the brain decreases more rapidly than in general aging (denaturation). About 5% of the population of those aged 65 years or over are said to be dementia patients; 40% of which being Alzheimer-type, and the number of patients is the highest among the diseases associated with denaturation of nerve. The number of patients is expected to increase in the future aging society, and the treatment thereof will become more and more important. The action of donepezil on Alzheimer-type dementia is considered to be based on an increase in brain acetylcholine, which is achieved mainly by the inhibition of acetylcholinesterase and activation of the brain cholinergic nerve system.

Conventionally, donepezil is mainly administered orally, and has been marketed in the dosage form of tablet, jelly and the like. However, patients with worsened symptoms of dementia have difficulty in orally taking the medicine. Therefore, administration of donepezil by a pathway other than oral one, particularly, transdermal administration using a transdermal absorption preparation, has been desired.

Patent document 5 describes use of an ester of fatty acid and lower alcohol such as diisopropyl adipate and the like to promote transdermal absorption of donepezil and the like in transdermal absorption preparations. Patent document 6 describes use of acetate salt to improve transdermal absorbability of donepezil hydrochloride in transdermal absorption preparations. However, the methods disclosed in these documents fail to provide good transdermal absorbability. On the other hand, patent document 7 describes use of a higher fatty acid salt to improve transdermal absorbability of donepezil hydrochloride in transdermal absorption preparations and achieves comparatively good transdermal absorbability. In some cases, however, crystals were precipitated from the preparation during storage, resulting in a decrease in adhesive property, an increase in skin irritation, and a decrease in transdermal absorbability.

DOCUMENT LIST

Patent Documents patent document 1: JP-A-2001-302502
patent document 2: JP-A-9-291028
patent document 3: JP-A-10-316559
patent document 4: WO 2012/029325
patent document 5: JP-A-11-315016
patent document 6: WO 2003/032960
patent document 7: WO 2013/035850

SUMMARY OF THE INVENTION

Problems to be Solved by the Invention

It is an object of the present invention to provide a transdermal absorption preparation having sufficient drug solubility, transdermal permeability, and sufficient adhesiveness to the skin, and showing low skin irritation. In particular, the present invention aims to provide a transdermal absorption preparation showing good transdermal absorbability of donepezil.

Means of Solving the Problems

The present inventors have conducted intensive studies in an attempt to solve the aforementioned problems and found that a transdermal absorption preparation having sufficient adhesiveness to the skin, sufficient drug solubility and transdermal absorbability can be obtained without using a tackifier but by using a thermoplastic elastomer and a fatty acid ester as adhesive bases, which resulted in the completion of the present invention.

They have also found that, when the drug is donepezil, the transdermal absorbability of donepezil can be further improved by adding long chain fatty acid (higher fatty acid) together with donepezil to the above-mentioned adhesive base.

The present invention based on these findings is as described below.

[1] A transdermal absorption preparation comprising a support and a drug-containing adhesive layer formed on the support, wherein the drug-containing adhesive layer comprises a thermoplastic elastomer and a higher fatty acid ester,
 a content of the higher fatty acid ester in the drug-containing adhesive layer is more than 50 parts by weight and not more than 500 parts by weight per 100 parts by weight of the thermoplastic elastomer, and
 a content of a tackifier in the drug-containing adhesive layer is not more than 10 wt % (0 wt % inclusive) relative to a total amount of the drug-containing adhesive layer.

[2] The transdermal absorption preparation of the above-mentioned [1], wherein a higher fatty acid in the higher fatty acid ester has a carbon number of not less than 12 and not more than 30.

[3] The transdermal absorption preparation of the above-mentioned [1] or [2], wherein the thermoplastic elastomer comprises a styrene-based block copolymer.

[4] The transdermal absorption preparation of the above-mentioned [3], wherein the styrene-based block copolymer is a styrene-isoprene-styrene block copolymer.

[5] The transdermal absorption preparation of any one of the above-mentioned [1] to [4], wherein the drug-containing adhesive layer does not contain a tackifier.

[6] The transdermal absorption preparation of any one of the above-mentioned [1] to [5], wherein the drug-containing adhesive layer comprises polyisobutylene.

[7] The transdermal absorption preparation of any one of the above-mentioned [1] to [6], wherein the drug-containing adhesive layer comprises donepezil or a salt thereof as the drug.

[8] The transdermal absorption preparation of the above-mentioned [7], wherein the drug-containing adhesive layer comprises donepezil or a salt thereof, and higher fatty acid.

[9] The transdermal absorption preparation of the above-mentioned [8], wherein the higher fatty acid has a carbon number of not less than 12 and not more than 30.

[10] The transdermal absorption preparation of the above-mentioned [8], wherein the higher fatty acid comprises oleic acid.

Effect of the Invention

The transdermal absorption preparation of the present invention is superior in drug solubility and releasability, as well as adhesiveness to the skin and low irritation to the skin.

In addition, the donepezil-containing transdermal absorption preparation of the present invention shows superior transdermal absorbability of donepezil.

DESCRIPTION OF EMBODIMENTS

Figure 1:
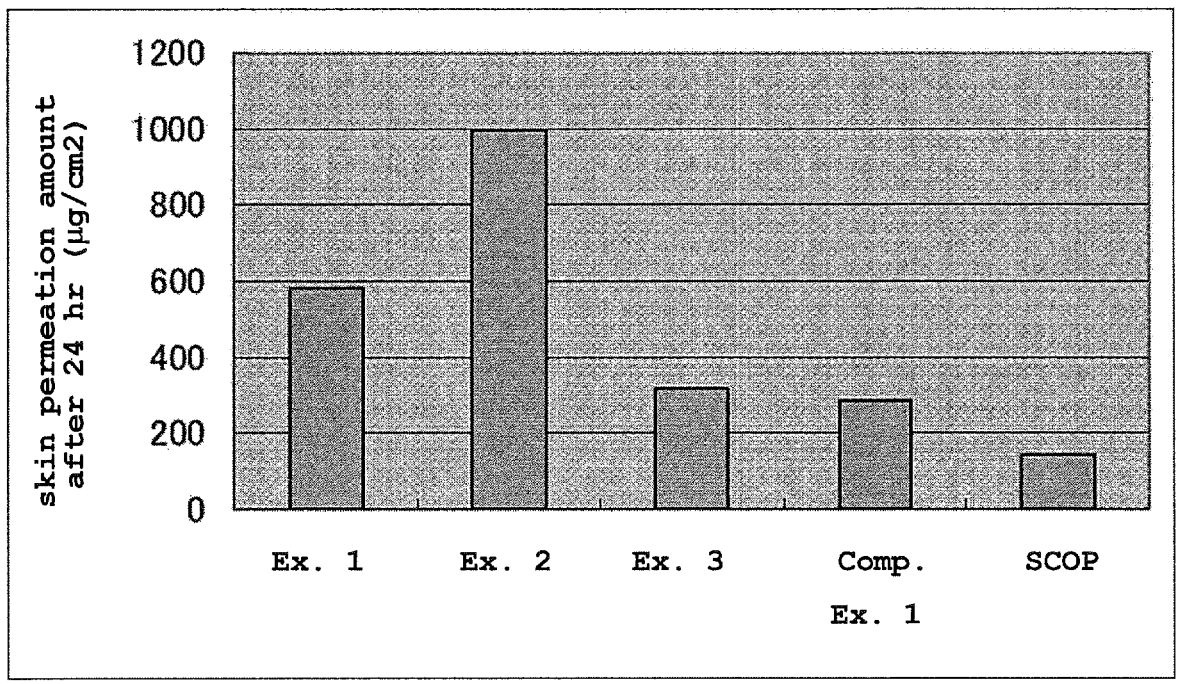
FIG. 1 is a graph showing transdermal permeation amount of scopolamine after 24 hr in in vitro transdermal permeation tests of Examples 1-3, Comparative Example 1 and commercially available scopolamine-containing transdermal absorption preparation.

The transdermal absorption preparation of the present invention is a transdermal absorption preparation comprising a support and a drug-containing adhesive layer (hereinafter to be also simply abbreviated as "adhesive layer") formed on the support, wherein the adhesive layer comprises a thermoplastic elastomer and a higher fatty acid ester, a content of the higher fatty acid ester in the drug-containing adhesive layer is more than 50 parts by weight and not more than 500 parts by weight per 100 parts by weight of the thermoplastic elastomer, and a content of a tackifier in the drug-containing adhesive layer is not more than 10 wt % (0 wt % inclusive) relative to a total amount of the drug-containing adhesive layer.

In addition, the transdermal absorption preparation of the present invention is characterized by an embodiment wherein the drug-containing adhesive layer contains donepezil or a salt thereof, and higher fatty acid.

The transdermal absorption preparation of the present invention contains a thermoplastic elastomer and a higher fatty acid ester, wherein
 the content of higher fatty acid ester in the drug-containing adhesive layer is preferably more than 50 parts by weight and not more than 500 parts by weight, per 100 parts by weight of the thermoplastic elastomer, and the content of a tackifier in the drug-containing adhesive layer is preferably not more than 10 wt % (0 wt % inclusive). Using such a large amount of higher fatty acid ester, good adhesiveness can be achieved even when the content of a tackifier in the drug-containing adhesive layer is limited to 10 wt % or below. By limiting the content of the tackifier, a transdermal absorption preparation showing less skin irritation can be obtained. In addition, the presence of a large amount of higher fatty acid ester also improves transdermal absorbability of the drug, further improves solubility of the drug, and can suppress, for example, crystallization thereof.

The "thermoplastic elastomer" to be used for the drug-containing adhesive layer of the present invention is an elastomer having thermoplasticity wherein it is softened when heat is added to show flowability, and returns to a rubbery elastic body by cooling, and various thermoplastic elastomers of urethane, acrylic, styrene, olefin series and the like can be mentioned. In the present invention, moreover, a mixture of a triblock copolymer and a diblock copolymer, wherein the content of the diblock copolymer in the mixture is not less than 20 wt %, is preferably used as the thermoplastic elastomer in order to impart sufficient skin adhesiveness to the adhesive sheet and transdermal absorption preparation. When the mixing ratio of the diblock copolymer is too low, skin adhesiveness tends to decrease. When it is too high, shape retention of the drug-containing adhesive layer tends to be degraded, which in turn may cause inconveniences on adhesion to the skin, such as adhesive residue on the skin after peeling off and the like. Therefore, the mixing ratio of the triblock copolymer and the diblock copolymer [(triblock copolymer)/(diblock copolymer)] is preferably 20/80-75/25, further more preferably 30/70-70/30, in weight ratio.

Particularly, a solution viscosity of a 25 wt % toluene solution of the thermoplastic elastomer at 25° C. is preferably not less than 0.5 Pa·s, further preferably not less than 0.7 Pa·s, particularly preferable not less than 0.9 Pa's, to afford a good balance of the adhesive property of the obtained adhesive sheet for skin adhesion and adhesive property of transdermal absorption preparation etc. (balance of adhesiveness and easy detachability). While the upper limit of the solution viscosity is not particularly limited, it is preferably not more than 2.0 Pa's, more preferably not more than 1.8 Pa's.

As used herein, the "solution viscosity of a 25 wt % toluene solution at 25° C." is a value measured based on "the viscosity measurement method of a styrene-isoprene-styrene block copolymer" described on page 375 of "Japanese Pharmaceutical Excipients 2003" (published by YAKUJI NIPPO LIMITED).

A styrene-based thermoplastic elastomer, particularly, styrene-based block copolymer is preferably used as the thermoplastic elastomer to simultaneously achieve sufficient skin adhesiveness and low skin irritation, which is the object of the present invention. Examples of the styrene-based block copolymer include a styrene-butadiene block copolymer, a styrene-butadiene-styrene block copolymer, a styrene-isoprene block copolymer, a styrene-isoprene-styrene block copolymer, a styrene-ethylene/butylene block copolymer, a styrene-ethylene/butylene-styrene block copolymer, a styrene-ethylene/propylene block copolymer, a styrene-ethylene/propylene-styrene block copolymer, a styrene-isobutylene block copolymer, a styrene-isobutylene-styrene block copolymer and the like. In the above, "ethylene/butylene" shows an ethylene and butylene copolymer block, and "ethylene/propylene" shows an ethylene and propylene copolymer block. In these styrene-based block copolymers, a triblock copolymer and a diblock copolymer can be preferably used in combination at the above-mentioned mixing ratio of the triblock copolymer and the diblock copolymer, and three or more kinds may be used in combination. That is, one or more kinds each of the triblock copolymer and diblock copolymer can be used.

From the aspects of simultaneous achievement of sufficient skin adhesiveness and low skin irritation, and availability and handling property of the products for adhesive skin preparation, of the above-mentioned styrene-based block copolymers, a mixture comprising a styrene-isoprene-styrene block copolymer and a styrene-isoprene block copolymer is preferably used. Particularly, a mixture of a styrene-isoprene-styrene block copolymer and a styrene-isoprene block copolymer is preferably used from the aspect of adhesiveness.

For the object of the present invention, a styrene-isoprene-styrene block copolymer preferably has a content of the styrene in the copolymer of 5 wt %-60 wt %, more preferably 10 wt %-50 wt %. In addition, it preferably has a weight average molecular weight as measured by gel permeation chromatography of not less than 20,000 and not more than 500,000, more preferably not less than 30,000 and not more than 300,000. The styrene-isoprene block copolymer preferably has a content of the styrene in the copolymer of not less than 5 wt % and not more than 50 wt %, more preferably not less than 10 wt % and not more than 40 wt %. In addition, it preferably has a weight average molecular weight as measured by gel permeation chromatography of not less than 10,000 and not more than 500,000, more preferably not less than 20,000 and not more than 300,000. The mixture of the styrene-isoprene-styrene block copolymer and the styrene-isoprene block copolymer preferably has a weight average molecular weight as measured by gel permeation chromatography of not less than 20,000 and not more than 500,000, more preferably not less than 30,000 and not more than 300,000.

As the styrene-isoprene-styrene block copolymer and the styrene-isoprene block copolymer, copolymers produced by a method known per se can be respectively used. As the styrene-isoprene-styrene block copolymer and the styrene-isoprene block copolymer, commercially available products that satisfy the above-mentioned properties can be respectively used. In addition, a mixture of the styrene-isoprene-styrene block copolymer and the styrene-isoprene block copolymer is also commercially available, and a commercially available product of a mixture of the styrene-isoprene-styrene block copolymer and the styrene-isoprene block copolymer, satisfying the above-mentioned properties, at the above-mentioned mixing ratio can be preferably used.

Examples of the commercially available product include "KRATON D1111", "KRATON D1163", "KRATON D1113" and "KRATON D1119" manufactured by KRATON POLYMERS, "JSR SIS5002", "JSR SIS5229", "JSR SIS5403" and "JSR SIS5505" manufactured by JSR, "Quintac 3421", "Quintac 3433N", "Quintac 3520", "Quintac 3450" and "Quintac 3270" manufactured by Nippon Zeon Co., Ltd. and the like. Of these, "KRATON D1163", "KRATON D1113", "JSR SIS5403", "JSR SIS5505", "Quintac 3433N", "Quintac 3520" are preferably used, and "JSR SIS5505", "Quintac 3520" are particularly preferably used from the aspects of the mixing ratio of the above-mentioned triblock copolymer and diblock copolymer, and solution viscosity.

When the content of the thermoplastic elastomer in the drug-containing adhesive layer is too small, the shape of the drug-containing adhesive layer is difficult to maintain, and when it is too much, skin adhesiveness tends to be insufficient. Therefore, the content of the thermoplastic elastomer in the drug-containing adhesive layer of the transdermal absorption preparation of the present invention is preferably not less than 8 wt %, more preferably not less than 10 wt %, further preferably not less than 12 wt %, particularly preferably not less than 15 wt %. In addition, not more than 44 wt % is preferable, not more than 42 wt % is more preferable, not more than 40 wt % is further preferable, and not more than 35 wt % is particularly preferable.

In a more specifically preferable embodiment, the content of the thermoplastic elastomer in the drug-containing adhesive layer is, for example, 8 wt %-44 wt %, more preferably 8 wt %-42 wt %, particularly preferably 10 wt %-40 wt %.

In the present invention, higher fatty acid ester is a compound in which a carboxyl group of higher fatty acid forms an ester bond with aliphatic alcohol. Higher fatty acid ester moderately plasticizes a thermoplastic elastomer, contributes to imparting tackiness, and has appropriate affinity with the drug, thereby improving drug solubility, preventing crystal precipitation, and improving transdermal absorbability.

In the present invention, the "fatty acid" refers to, as described in RIKAGAKU JITEN (physics and chemistry dictionary) 5th Edition (IWANAMI SHOTEN), a chain monocarboxylic acid, the "higher fatty acid" refers to a fatty acid having a carbon number of not less than 10, and the "lower fatty acid" refers to a fatty acid having a carbon number of not more than 9.

The higher fatty acid constituting higher fatty acid ester may be a linear or branched chain. While higher fatty acid may be saturated or unsaturated, saturated fatty acid is preferable from the aspects of the plasticizing effect of the thermoplastic elastomer and thermal stability. The carbon number of higher fatty acid is preferably not less than 12, more preferably not less than 14, further preferably not less than 16, and preferably not more than 30, more preferably not more than 24, further preferably not more than 20.

Examples of the saturated higher fatty acid include capric acid (carbon number 10), lauric acid (carbon number 12), myristic acid (carbon number 14), palmitic acid (carbon number 16), stearic acid (carbon number 18), isostearic acid (carbon number 18), arachidic acid (carbon number 20), behenic acid (carbon number 22), lignoceric acid (carbon number 24), cerotic acid (carbon number 26), montanic acid (carbon number 28), melissic acid (carbon number 30) and the like. Of these, myristic acid, palmitic acid or stearic acid is preferable.

Examples of the unsaturated higher fatty acid include palmitoleic acid (carbon number 16), oleic acid (carbon number 18), linoleic acid (carbon number 18), (9,12,15)-linolenic acid (carbon number 18), (6,9,12)-linolenic acid (carbon number 18), eleostearic acid (carbon number 18) and the like. Of these, oleic acid and linoleic acid are preferable, and oleic acid is more preferable.

As aliphatic alcohol constituting higher fatty acid ester, saturated or unsaturated aliphatic alcohol having a carbon number of 1-20 is preferable. For example, methanol, ethanol, propanol, isopropanol, butanol, hexanol, pentanol, heptanol, octanol, decanol, cetanol, myristyl alcohol, hexyldecanol, oleyl alcohol, octyldodecanol and the like can be mentioned.

Specific preferable examples of the higher fatty acid ester include myristic acid esters such as isopropyl myristate, ethyl myristate, octyldodecyl myristate and the like, palmitic acid esters such as isopropyl palmitate, ethyl palmitate and the like, stearic acid esters such as isopropyl stearate and the like, oleic acid esters such as decyl oleate, octyldodecyl oleate, oleyl oleate and the like, linoleic acid esters such as ethyl linoleate and the like, and the like.

The content of higher fatty acid ester in the drug-containing adhesive layer is preferably more than 50 parts by weight and not more than 500 parts by weight, more preferably not less than 100 parts by weight and not more than 300 parts by weight, per 100 parts by weight of the thermoplastic elastomer. When the amount of higher fatty acid ester is too small, good adhesiveness or drug solubility cannot be achieved and, conversely, when too much higher fatty acid esters are present, it is difficult to maintain the shape of the adhesive layer.

To reduce skin irritation, and the like, the content of the tackifier in the drug-containing adhesive layer is preferably not more than 10 wt %, more preferably not more than 8 wt %, further preferably not more than 6 wt %, particularly preferably not more than 3 wt %. It is most preferable that the drug-containing adhesive layer be free of a tackifier (i.e., tackifier content being 0 wt %).

Tackifier is well known in the field of transdermal absorption preparations and generally means a resin used to impart adhesiveness to or improve adhesiveness of the adhesive base forming the adhesive layer. Examples of the tackifier include rosin resin, polyterpene resin, chroman-indene resin, petroleum resin, terpene resin, terpene-phenol resin, alicyclic saturated hydrocarbon resin and the like.

In the present invention, it is preferable to add polyisobutylene to adjust adhesive properties. The "polyisobutylene" used in the drug-containing adhesive layer of the present invention is a polymer of isobutylene, which is an elastic rubbery semisolid or viscous substance, and added in the present invention to impart sufficient skin adhesiveness to the transdermal absorption preparation.

For the object of the present invention, as polyisobutylene, low-molecular-weight polyisobutylene having a viscosity average molecular weight of 30,000-100,000, middle-molecular-weight polyisobutylene having a viscosity average molecular weight of 100,000-500,000, and high-molecular-weight polyisobutylene having a viscosity average molecular weight of 500,000-5,000,000 can be used each singly or in a mixture. Particularly, it is preferable to use a mixture of low-molecular-weight polyisobutylene and high-molecular-weight polyisobutylene, or middle-molecular-weight polyisobutylene singly, to afford well-balanced low skin irritation and high skin adhesiveness.

As polyisobutylene, an isobutylene polymer produced by a method known per se can be used. Particularly, in an adhesive layer of the present invention which is for attachment to skin, those compatible with the standard defined in the Japanese Pharmaceutical Excipients, the United States Pharmacopeia and the like, and the like can be preferably used. As polyisobutylene, commercially available products each meeting the above-mentioned viscosity average molecular weight can be used.

As commercially available products, examples of low-molecular-weight polyisobutylene include "Oppanol B10SFN", "Oppanol B10N", "Oppanol B12SFN", "Oppanol B15SFN", "Oppanol B15N" manufactured by BASF and the like, examples of middle-molecular-weight polyisobutylene include "Oppanol 330SF", "Oppanol B50SF", "Oppanol B50" manufactured by BASF and the like, and examples of the high-molecular-weight polyisobutylene include "Oppanol B80", "Oppanol B100", "Oppanol B150", "Oppanol B200" manufactured by BASF and the like. Of these, "Oppanol B15SFN" and "Oppanol B15N" having a viscosity average molecular weight of 50,000-100,000 are particularly preferably used as low-molecular-weight polyisobutylene, "Oppanol B50SF" and "Oppanol B50" are particularly preferably used as middle-molecular-weight polyisobutylene, and "Oppanol B80" is particularly preferably used as high-molecular-weight polyisobutylene, from the aspects of the solubility when forming a coating solution and the balance of the adhesive physical properties of the obtained adhesive sheet and transdermal absorption preparation.

When the content of polyisobutylene in the adhesive layer is too small, enhancement of the skin adhesiveness becomes insufficient. When the content is too high, exacerbation of skin irritation due to excessive enhancement of the skin adhesiveness, adhesive residue on peeling off, poor drug dissolution and the like sometimes pose problems. Therefore, the content of polyisobutylene in the drug-containing adhesive layer of the transdermal absorption preparation of the present invention is not less than 0.1 part by weight, preferably not less than 0.3 parts by weight, more preferably not less than 0.5 parts by weight, further preferably not less than 1 part by weight, per 100 parts by weight of the thermoplastic elastomer. It is also not more than 300 parts by weight, preferably not more than 100 parts by weight, more preferably not more than 50 parts by weight, further preferably not more than 30 parts by weight, per 100 parts by weight of the thermoplastic elastomer.

In a more specific and preferable embodiment, the content of polyisobutylene in the drug-containing adhesive layer is 0.1 wt %-50 wt %, more preferably 0.2 wt %-40 wt %, further preferably 0.3 wt %-30 wt %, particularly preferably 0.5 wt %-25 wt %.

The "drug or a pharmaceutically acceptable salt thereof" in the present invention refers to a drug or a pharmaceutically acceptable salt thereof to be used for transdermal absorption, and is not particularly limited. Examples of the drug include anti-inflammatory agents such as acetaminophen, phenacetin, mefenamic acid, diclofenac sodium, flufenamic acid, aspirin, sodium salicylate, methyl salicylate, glycol salicylate, aminopyrine, alclofenac, ibuprofen, naproxen, flurbiprofen, ketoprofen, amfenac sodium, mepirizole, indomethacin, piroxicam, felbinac and the like; steroidal anti-inflammatory drugs such as hydrocortisone, triamcinolone, dexamethasone, predonisolone and the like; vasodilators such as diltiazem hydrochloride, pentaerythritol tetranitrate, isosorbide nitrate, tradipil, nicorandil, nitroglycerol, prenylamine lactate, molsidomine, amyl nitrite, tolazoline hydrochloride, nifedipine and the like; antiarrhythmic agents such as procaineamide hydrochloride, lidocaine hydrochloride, propranolol hydrochloride, alprenolol hydrochloride, atenolol, nadolol, metoprolol tartrate, ajmaline, disopyramide, mexiletine hydrochloride and the like; antihypertensive agents such as ecarazine hydrochloride, indapamide, clonidine hydrochloride, bunitrolol hydrochloride, labetalol hydrochloride, captopril, guanabenz acetate, mebutamate, bethanidine sulfate and the like; antitussive expectorants such as carbetapentane citrate, cloperastine, oxeladin tannate, cloputinol hydrochloride, clofedanol hydrochloride, noscapine hydrochloride, ephedrine hydrochloride, isoproterenol hydrochloride, cloriprenaline hydrochloride, methoxyphenamine hydrochloride, procaterol hydrochloride, tulobuterol hydrochloride, clenputerol hydrochloride, ketotifen fumarate and the like; antineoplastic drugs such as cyclophosphamide, fluorouracil, degafur, mitomycin C, procarbazine hydrochloride, doxifluridine, ranimustine and the like; local anesthetics such as ethyl aminobenzoate, tetracaine hydrochloride, procaine hydrochloride, dibucaine hydrochloride, oxybuprocaine hydrochloride, propitocaine hydrochloride and the like; hormone preparations such as propylthiouracil, thiamazole, metelonone acetate, estradiol, estriol, progesterone and the like; antihistamine agents such as diphenhydramine hydrochloride, chlorpheniramine maleate, promethazine, dyproheptadine hydrochloride, diphenylpyraline hydrochloride and the like; anticoagulants such as warfarin potassium, ticlopidine hydrochloride and the like; anticonvulsive agents such as atropine methylbromide, scopolamine and the like; general anesthetics such as thiopental sodium, pentobarbital sodium and the like; hypnotics or analgesics such as bromovalenylurea, amobarbital, phenobarbital and the like; antiepileptic agents such as phenytoin sodium and the like; analeptics or stimulant drugs such as methamphetamine hydrochloride and the like; antidizziness drugs such as difendol hydrochloride, betahistine mesilate and the like; psychoneurotic agents such as chlorpromazine hydrochloride, thioridazine, meprobamate, imipramine hydrochloride, chlordiazepoxide, diazepam, risperidone, paliperidone, olanzapine, aripiprazole, paroxetine, duloxetine and the like; muscle relaxants such as suxamethonium chloride, eperisone hydrochloride and the like; autonomic agents such as neostigmine bromide, bethanechol chloride and the like; antiparkinson agents such as amantadine hydrochloride, rotigotine, ropinirole and the like; anti Alzheimer-type dementia agents such as donepezil, galanthamine, memantine, rivastigmine and the like; diuretics such as hydroflumethiazide, isosorbide, furosemide and the like; vasoconstrictors such as phenylephrine hydrochloride and the like; respiratory stimulants such as lobeline bromide, dimorpholamine, naloxone hydrochloride and the like; peptic ulcer therapeutic agents such as glycopyrronium bromide, proglumide, cetraxate hydrochloride, cimetidine, spizofurone and the like; cholagogues such as ursodesoxycholic acid, osalmid and the like; urogenital and anus agents such as hexamine, sparteine, dinoprost, ritodrine hydrochloride, oxybutynin, tolterodine, solifenacin, darifenacin and the like; agents for parasitic skin diseases such as salicylic acid, ciclopirox olamine, coroconazole hydrochloride and the like; skin softeners such as urea and the like; vitamins such as calcitriol, thiamine hydrochloride, riboflapin sodium phosphate, pyridoxine hydrochloride, nicotinamide, panthenol, ascorbic acid and the like; mineral preparations such as calcium chloride, potassium iodide, sodium iodide and the like; hemostatic drugs such as ethamsylate and the like; agents for liver diseases such as tiopronin and the like; agents for habitual intoxication such as cyanamide and the like; therapeutic agents for gout such as colchicine, probenecid, sulfinpyrazone and the like; diabetic agents such as tolbutamide, chlorpropamide, glymidine sodium, glypuzole, puformin hydrochloride, insulin and the like; antibiotics such as benzylpenicillin potassium, propicillin potassium, cloxacillin sodium, ampicillin sodium, bacampillicin hydrochloride, carbenicillin sodium, cephaloridine, cefoxitin sodium, erythromycin, chloramphenicol, tetracycline, kanamycin sulfate, cycloserine and the like; chemotherapeutic agents such as isocyanide, pyrazinamide, ethionamide and the like; narcotics such as morphine hydrochloride, codeine phosphate, cocaine hydrochloride, pethidine hydrochloride, fentanyl citrate and the like; and the like. As pharmaceutically acceptable salts of these drugs, not only the above-mentioned salts but also various salts can be used, and the drugs in a free form can also be used.

As one of the typical examples of the drug in the transdermal absorption preparation of the present invention, donepezil or a salt thereof (pharmacologically acceptable salt) can be mentioned. Donepezil refers to 1-benzyl-4-(5, 6-dimethoxyindanon-2-yl)methylpiperidine. The drug-containing adhesive layer may contain both donepezil and a salt thereof. In addition, one kind of donepezil salt may be used, or two or more kinds thereof may be used in combination. From the aspects of easy availability and the like, donepezil or a salt thereof is preferably donepezil (free form of donepezil).

The content of donepezil or a salt thereof (when they are use in combination, the total amount thereof) in the drug-containing adhesive layer is preferably 0.5-20 wt %, more preferably 1-15 wt %, further preferably 2-10 wt %, particularly preferably 2.5-7.5 wt %, to ensure dispersibility in a drug-containing adhesive layer and good transdermal absorbability, though the present invention is not limited thereto.

One of the characteristics of the present invention is use of a higher fatty acid to improve transdermal absorbability of donepezil. The "higher fatty acid" herein is used as a separate component from the aforementioned "higher fatty acid ester".

The higher fatty acid may be a linear or branched chain. It may be saturated or unsaturated. The carbon number of higher fatty acid is preferably not less than 12, more preferably not less than 14, further preferably not less than 16, and preferably not more than 30, more preferably not more than 24, further preferably not more than 20.

Examples of the saturated higher fatty acid include capric acid (carbon number 10), lauric acid (carbon number 12), myristic acid (carbon number 14), palmitic acid (carbon number 16), stearic acid (carbon number 18), isostearic acid (carbon number 18), arachidic acid (carbon number 20), behenic acid (carbon number 22), lignoceric acid (carbon number 24), cerotic acid (carbon number 26), montanic acid (carbon number 28), melissic acid (carbon number 30) and the like.

Examples of the unsaturated higher fatty acid include palmitoleic acid (carbon number 16), oleic acid (carbon number 18), linoleic acid (carbon number 18), (9,12,15)-linolenic acid (carbon number 18), (6,9,12)-linolenic acid (carbon number 18), eleostearic acid (carbon number 18) and the like.

Of these, higher fatty acid which is liquid at ambient temperature is preferable, more preferably at least one selected from the group consisting of oleic acid, isostearic acid and linoleic acid, further more preferably at least one selected from the group consisting of oleic acid, and isostearic acid, particularly preferably oleic acid.

The content of the higher fatty acid in a drug-containing adhesive layer is preferably not less than 0.1 mol, more preferably not less than 0.2 mol, further preferably not less than 0.3 mol, particularly preferably not less than 0.5 mol, and preferably not more than 5 mol, more preferably not more than 3 mol, further preferably not more than 2 mol, per 1 mol of donepezil, though the present invention is not limited thereto. When the amount of higher fatty acid is too small, a sufficient transdermal absorbability improving effect cannot be obtained. Conversely, when the amount of higher fatty acid is too high, the preparation property such as adhesive property and the like may be degraded.

To further improve transdermal absorbability of a drug, the drug-containing adhesive layer preferably contains an ester solvent.

Examples of the ester solvent include triacetine, medium chain fatty acid ester, an ester of polyvalent carboxylic acid and monovalent aliphatic alcohol, an ester of polyhydric alcohol and monovalent fatty acid, carbonate ester and the like.

Examples of the medium chain fatty acid ester include monoalcohol ester of medium chain fatty acid such as ethyl 2-ethylhexanoate, cetyl 2-ethylhexanoate and the like, medium-chain triglyceride and the like. Examples of the medium-chain triglyceride include caprylic acid triglyceride, caproic acid triglyceride and the like. Examples of the fats and oils containing high medium-chain triglyceride include peanuts oil, olive oil, castor oil and the like. Examples of the ester of polyvalent carboxylic acid and monovalent aliphatic alcohol include sebacic acid ester such as diethyl sebacate, diisopropyl sebacate and the like, and adipic acid ester such as diethyl adipate, diisopropyl adipate and the like. Examples of the ester of polyhydric alcohol and monovalent fatty acid include fatty acid ester of ethylene glycol and propylene glycol, and examples of the carbonate ester include propylene carbonate and the like. Of these, cetyl 2-ethylhexanoate, medium-chain triglyceride, sebacic acid ester, adipic acid ester, carbonate ester is preferable, diisopropyl adipate or cetyl 2-ethylhexanoate is more preferable.

In the present invention, moreover, it is preferable to add liquid paraffin to adjust adhesiveness or improve coating property. In the present invention, the liquid paraffin refers to paraffin having a kinematic viscosity at 40° C. of 0.1-10000 cSt as measured according to ASTM D-445. The liquid paraffin is generally a mixture of alkane which is liquid at ambient temperature and has a carbon number of not less than 20. As the liquid paraffin, a commercially available product, particularly, one compatible with the pharmaceutical product-related standards defined in the Japanese Pharmacopoeia, the United States Pharmacopeia and the like can be preferably used. For example, liquid paraffin is commercially available from Sonneborn under the trade name of "KAYDOL".

The transdermal absorption preparation of the present invention has a support provided with a drug-containing adhesive layer. The support in the present invention is not particularly limited, and a support widely used in the art can be used. Examples of the support include stretchable or unstretchable woven fabric of polyethylene, polypropylene and the like; non-woven fabric; film of polyethylene, polypropylene, ethylene vinyl acetate copolymer, vinyl chloride, polyester (e.g., poly(ethylene terephthalate) (PET)) and the like; foamed supports of urethane, polyurethane and the like; and the like. The support may be a single layer structure or a laminate structure. Furthermore, to prevent accumulation of static electricity, an antistatic agent may be applied to the support. To achieve good anchor property with an adhesive layer, a non-woven fabric or woven fabric is preferably used as a support. The thickness of the support is preferably not less than 10 μm, more preferably not less than 15 μm, preferably not more than 100 μm, more preferably not more than 50 μm for a film, and preferably not less than 50 μm, more preferably not less than 100 μm, preferably not more than 2000 μm, more preferably not more than 1000 μm for a porous sheet such as woven fabric, non-woven fabric, foamed support and the like.

The transdermal absorption preparation of the present invention may contain, as an optional component, surfactant, diluent, antioxidant, softening agent, flavor, colorant and the like. Only one kind of these optional components may be used, or two or more kinds thereof may be used in combination.

The surfactant may be any of anionic surfactant, nonionic surfactant, cationic surfactant and amphoteric surfactant. Examples of the surfactant include natural emulsifier, soap, polyoxyethylene sorbitan fatty acid ester, glycerine fatty acid ester, sorbitan fatty acid ester, polyoxyethylene higher alcohol ether, polyoxyethylene alkylphenol and the like.

Examples of the natural emulsifier include gum arabic, gelatin, tragacanth, lecithin, cholesterol and the like. Examples of the polyoxyethylene sorbitan fatty acid ester include monooleyl sorbitan polyoxyethylene and the like. Examples of the glycerine fatty acid ester include polyoxyethylene castor oil derivative, polyoxyethylene hydrogenated castor oil, glycerol monostearate and the like. Examples of the sorbitan fatty acid ester include sorbitan monostearate, sorbitan monolaurate, sorbitan monooleate, sorbitan sesquioleate, sorbitan trioleate and the like. As the polyoxyethylene higher alcohol ether, polyoxyethylene cetyl ether, polyoxyethylene dodecyl ether and the like can be mentioned. Examples of other surfactant include sodium alkyl sulfate (e.g., sodium lauryl sulfate etc.), polyoxyethylene polyoxypropylene copolymer (e.g., Pluronic etc.), cetyltrimethylammonium chloride and the like.

Examples of the diluent include silicon compound such as silicic anhydride, light anhydrous silicic acid, hydrous silicic acid and the like, cellulose derivative such as ethylcellulose, methylcellulose, hydroxypropylcellulose, hydroxypropylmethylcellulose and the like, water-soluble polymer such as poly(vinyl alcohol) and the like, aluminum compound such as dried aluminum hydroxide gel, hydrated aluminum silicate and the like, kaolin, titanium oxide and the like, and the like.

Examples of the antioxidant include dibutylhydroxytoluene, ascorbic acid, tocopherol, tocopherol ester derivative, butylhydroxyanisole, 2-mercaptobenzimidazole and the like.

The transdermal absorption preparation of the present invention can be produced by a method including dissolving or dispersing a drug, a thermoplastic elastomer, higher fatty acid ester and the like in a dilution solvent (e.g., toluene, tetrahydrofuran), preparing a coating solution for the formation of a drug-containing adhesive layer, applying the obtained coating solution on a support, and then drying same, i.e., so-called solution method. Application and drying of the coating solution for the formation of an adhesive layer can be performed by a means well known in the field of transdermal absorption preparation. Alternatively, it can also be produced by a method including heating and melt kneading a drug, a thermoplastic elastomer and higher fatty acid ester and the like, adjusting a coating solution, applying the obtained coating solution on a support, and then cooling same, i.e., so-called hot-melt method. The drug-containing adhesive layer after drying in the solution method and after cooling in the hot-melt method is preferably not less than 10 g/m², more preferably not less than 20 g/m², further preferably not less than 30 g/m², and preferably not more than 2000 g/m², more preferably not more than 1000 g/m², further preferably not more than 800 g/m².

It is also possible to form a release liner on the drug-containing adhesive layer of the transdermal absorption preparation of the present invention. When a release liner is used, the transdermal absorption preparation can also be produced by applying the aforementioned coating solution for the formation of an adhesive layer to a release liner and drying same to form a release liner provided with a drug-containing adhesive layer, and laminating a support on the drug-containing adhesive layer.

EXAMPLE

The present invention is explained in more detail in the following by referring to Examples and Comparative Examples, which are not to be construed as limitative. In the following, "parts" and "%" mean "parts by weight" and "wt %", unless specifically indicated otherwise.

Examples 1-3, Comparative Example 1

The amounts described in the following Table 1 were mixed with heating at 70° C.-100° C. and applied to a silicone-treated PET film (release liner). A PET film (support) was laminated on the surface of the obtained adhesive layer to give a laminated sheet. The laminated sheet was cut into a desired size to give the transdermal absorption preparations of Examples 1-3 and Comparative Example 1.

TABLE 1

| reagents | Example 1 | Example 2 | Example 3 | Comparative Example 1 |
|---|---|---|---|---|
| elastomer: | | | | |
| styrene-isoprene-styrene copolymer (SIS5505: manufactured by JSR) | 29.3 | 32.5 | 29.1 | 29.3 |
| liquid paraffin (Kaydol: manufactured by Sonneborn) | | | | 68.3 |
| higher fatty acid ester: | | | | |
| octyldodecyl myristate | 68.4 | 65.0 | 63.1 | |
| polyisobutylene: | | | | |
| Oppanol B-50 | | 1.4 | 4.9 | |
| scopolamine | 2.3 | 1.1 | 2.9 | 2.5 |
| total | 100.0 | 100.0 | 100.0 | 100.0 |

Experimental Example 1

Using Examples 1-3, Comparative Example 1, and a commercially available scopolamine-containing transdermal absorption preparation, Transderm SCOP (manufactured by Sandoz), the following in vitro transdermal permeation test was performed. An abdominal skin of male Wister rat (5-week-old) was set on a vertical Franz diffusion cell. Then, the transdermal absorption preparation was cut out in a circular shape with diameter 1.0 cm, the release liner was detached and the preparation was adhered to the rat skin on the diffusion cell (n=3). In the receptor side, using an ethanol-saline mixed solution (ethanol amount: 10%), the amount of scopolamine that permeated through the rat skin after a given time was measured by high performance liquid chromatography (HPLC) under the following measurement condition.

<HPLC Conditions>
  HPLC system: high performance liquid chromatogram (LC2010C) manufactured by SHIMADZU CORPORATION
  column: ODS, 4.6 mmφ×15 cm, filler particle size 5 μm
  column temperature: 40° C.
  mobile phase: 0.1% aqueous phosphoric acid solution/methanol/acetonitrile/SDS=4/1/5/0.01 (weight ratio)
  detection wavelength: 271 nm
  flow: 0.7 mL/min The permeation amount of scopolamine at 24 hr after adhesion is shown in FIG. 1. In addition, the relationship between transdermal permeation rate of scopolamine in rat and adhesion time in Example 3 and the commercially available scopolamine-containing transdermal absorption preparation is shown in FIG. 2.

Figure 2:
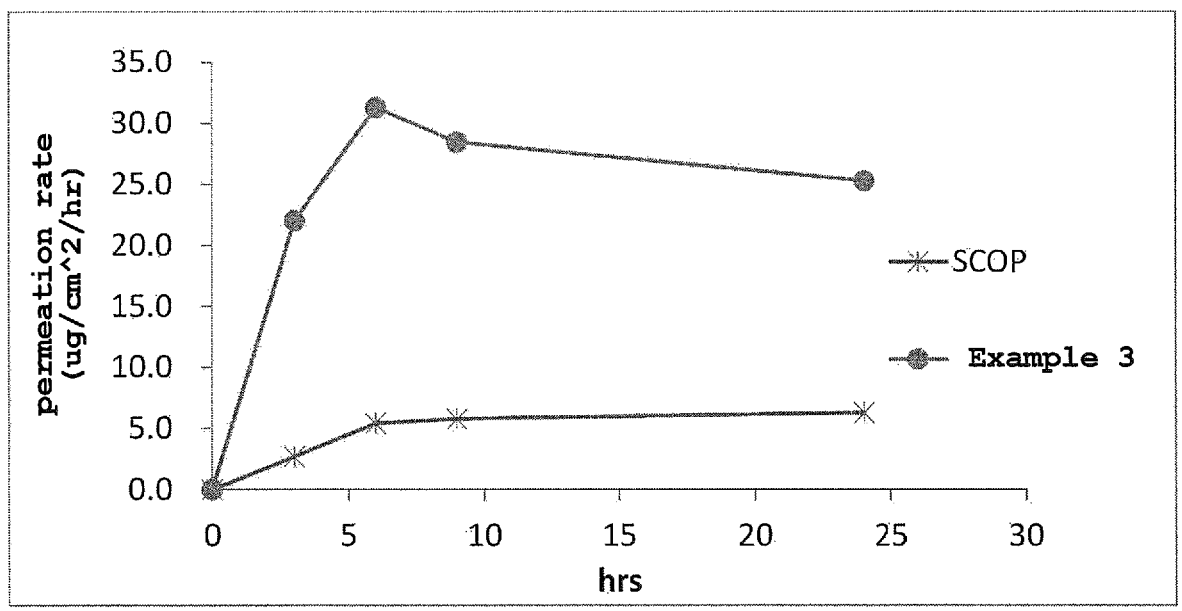
FIG. 2 is a graph showing relationship between transdermal permeation rate of scopolamine in rat and adhesion time in in vitro transdermal permeation test of Example 3 and commercially available scopolamine-containing transdermal absorption preparation.

From FIG. 1 and FIG. 2, it is clear that the transdermal absorption transdermal absorption preparation of the present invention shows high transdermal absorbability of scopolamine and maintains high absorbability for 24 hr. To be specific, compared to the transdermal absorption preparation of Comparative Example 1, the transdermal absorption preparation of Example 1 having almost the same concentration shows a high transdermal permeation amount. It has been found that the transdermal absorbability of the transdermal absorption preparation of Comparative Example 1 markedly decrease over time due to storage. As shown in FIG. 2, the transdermal absorption preparation of Example 3 showed a remarkably high permeation rate as compared to the commercially available product from 3 hr after the start of the test, and maintained a high permeation rate from after 6 hr to after 24 hr. It also showed a higher value of cumulative scopolamine transdermal permeation amount than the commercially available product.

Examples 4-5

The starting materials described in the following Table 2 in the amounts described in Table 2 were mixed with heating at 80° C.-105° C. and the mixture was applied to a silicone-treated PET film (release liner). A PET film (support) was laminated on the surface of the obtained adhesive layer to give a laminated sheet. The laminated sheet was cut into a desired size to give the transdermal absorption preparations of Examples 4-5.

Comparative Examples 2-4

A styrene-isoprene-styrene block copolymer ("JSR SIS5002", manufactured by JSR) and liquid paraffin ("KAYDOL", manufactured by Sonneborn) in the amounts described in the following Table 2 were dissolved in tetrahydrofuran (THF) to give a solution of a styrene-isoprene-styrene block copolymer and the like. Then, a fatty acid salt and donepezil hydrochloride in the amounts described in the following Table 2 were dissolved in an ester solvent and an alcohol solvent to give a solution of fatty acid salt and the like. The obtained solution of the styrene-isoprene-styrene block copolymer and the like and the solution of the fatty acid salt and the like were mixed to give a coating solution for forming of adhesive layer. The obtained coating solution for forming of adhesive layer was applied to a silicone-treated PET film (release liner) such that the amount of the drug-containing adhesive layer is 300 g/m² after drying. The release liner coated with the adhesive base was dried in an oven at 80° C. for 30 min, and a PET film (support) was laminated on the surface of the obtained adhesive layer to give a laminated sheet. The laminated sheet was cut into a desired size to give the transdermal absorption preparations of Comparative Examples 2-4. The transdermal absorption preparation of Comparative Example 4 using acetate salt showed crystallization and drug formulation was a failure.

TABLE 2

| Reagents | Example 4 | Example 5 | Comparative Example 2 | Comparative Example 3 | Comparative Example 4 |
|---|---|---|---|---|---|
| elastomer: | | | | | |
| styrene-isoprene-styrene copolymer | 26.0 | 24.0 | 10.0 | 10.0 | 10.0 |
| liquid paraffin | 2.5 | 2.4 | 68.0 | 63.0 | 67.0 |
| higher fatty acid ester: | | | | | |
| octyldodecyl myristate | 40.7 | 38.3 | | | |
| higher fatty acid: | | | | | |
| oleic acid | 3.7 | 6.1 | | | |
| polyisobutylene: | | | | | |
| Oppanol B-50 | 0.6 | 0.6 | | | |
| fatty acid salt: | | | | | |
| sodium acetate | | | | | 1.0 |
| ester solvent: | | | | | |
| diisopropyl adipate | 1.3 | 1.2 | 5.0 | 10.0 | 5.0 |
| cetyl 2-ethylhexanoate | 13.2 | 12.8 | | | |
| tackifier: | | | | | |
| terpene resin | 6.6 | 6.4 | | | |
| antioxidant: | | | | | |
| dibutylhydroxytoluene | 0.5 | 0.5 | | | |
| alcohol solvent: | | | | | |
| propylene glycol | | | 12.0 | 12.0 | 12.0 |
| donepezil free form | 5.0 | 7.7 | | | |
| donepezil hydrochloride | | | 5.0 | 5.0 | 5.0 |
| total | 100.0 | 100.0 | 100.0 | 100.0 | 100.0 |
| molar equivalent of fatty acid (salt) to donepezil | 1.0 | 1.0 | | | 1.0 |

Experimental Example 2

Using the transdermal absorption preparations of Examples 4-5 and Comparative Examples 2-4, the following in vitro transdermal permeation test was performed. An abdominal skin of male Wister rat (5-week-old) was set on a vertical Franz diffusion cell. Then, the transdermal absorption preparation was cut out in a circular shape with diameter 1.0 cm, the release liner was detached and the preparation was adhered to the rat skin on the diffusion cell (n=3). In the receptor side, using an ethanol-saline mixed solution (ethanol amount: 10%), the amount of donepezil that permeated through the rat skin after a given time was measured by high performance liquid chromatography (HPLC) under the following measurement conditions.

<HPLC Conditions>
HPLC system: high performance liquid chromatogram (LC2010C) manufactured by SHIMADZU CORPORATION
column: ODS, 4.6 mmφ×15 cm, 5 µm
column temperature: 40° C.
mobile layer: 0.1% aqueous phosphoric acid solution/methanol/acetonitrile/SDS=4/1/5/0.01 (weight ratio)

detection wavelength: 271 nm flow: 0.7 mL/min

Figure 3:
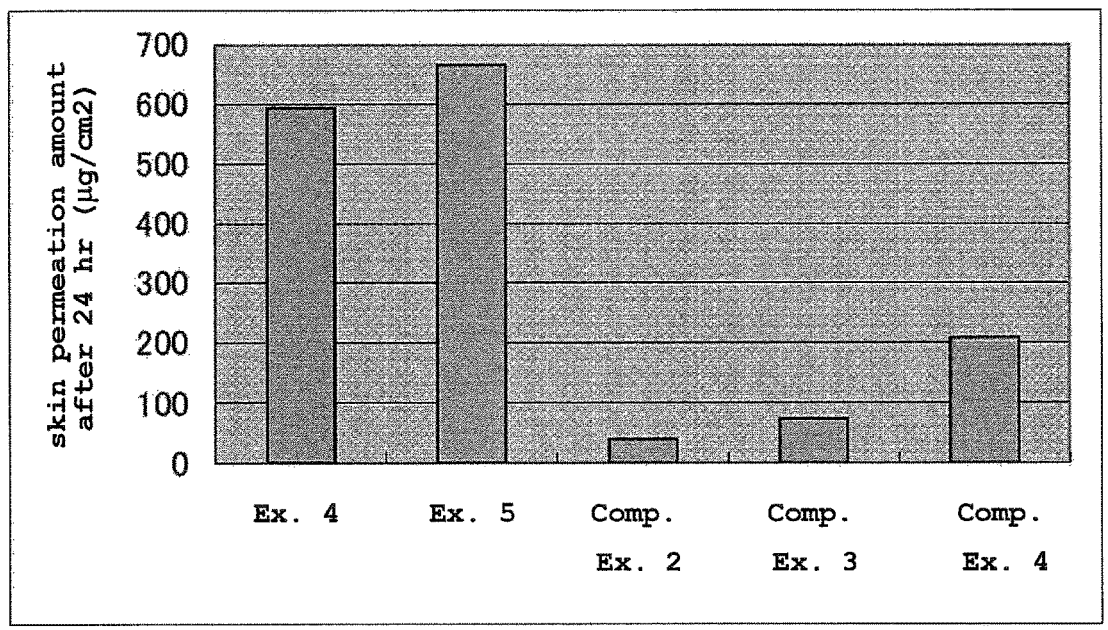
FIG. 3 is a graph showing transdermal permeation amount of donepezil after 24 hr in in vitro transdermal permeation tests of Examples 4-5 and Comparative Examples 2-4.

The permeation amount of donepezil at 24 hr after adhesion is shown in FIG. 3. In addition, the relationship between transdermal permeation rate of donepezil in rat and adhesion time in the donepezil-containing transdermal absorption preparation of Examples 4, 5 is shown in FIG. 4.

Figure 4:
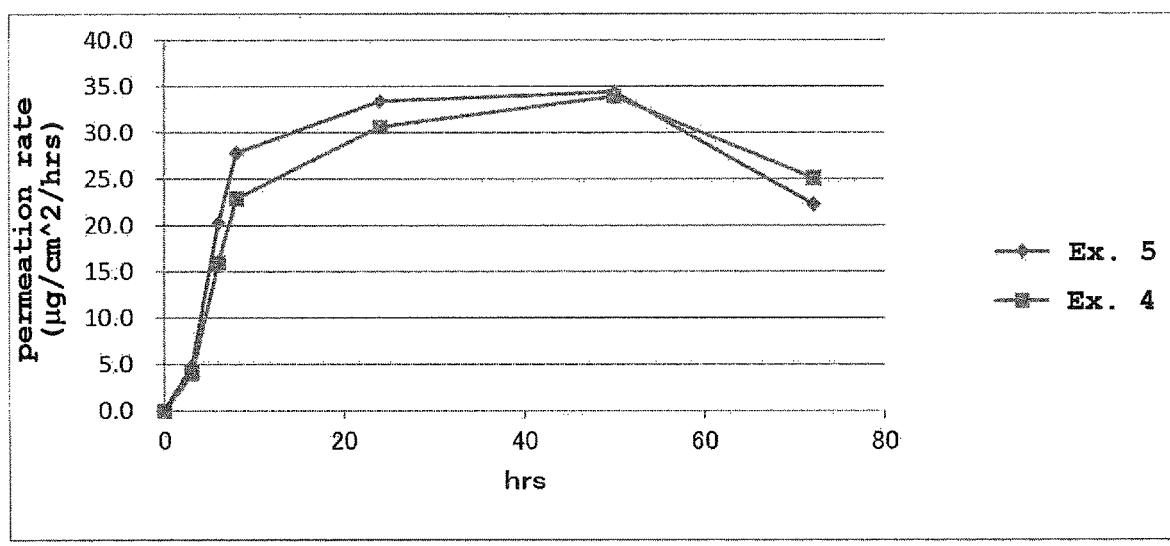
FIG. 4 is a graph showing relationship between transdermal permeation rate of donepezil in rat and adhesion time in in vitro transdermal permeation tests of Examples 4-5.

It is clear from FIG. 3 and FIG. 4 that the transdermal absorption transdermal absorption preparation of the present invention shows high transdermal absorbability of donepezil and maintained high absorbability for 3 days. To be specific, the transdermal absorption preparations of Examples 4-5 using a higher fatty acid ester and a higher fatty acid showed high transdermal permeation amounts of donepezil as compared to the transdermal absorption preparation of Comparative Example 3 using a high amount of diisopropyl adipate, which is described in patent document 5, and Comparative Example 4 using acetate salt, which is described in patent document 6.

In the transdermal absorption preparation of Comparative Example 4 using a lower fatty acid salt (acetate salt), crystal was precipitated from a drug-containing adhesive layer, and drug formulation was a failure. Such crystallization was not seen in the transdermal absorption preparations of Examples 4-5 using a higher fatty acid ester and higher fatty acid. It also demonstrates that a higher fatty acid ester and higher fatty acid is advantageously used for a donepezil-containing transdermal absorption preparation.

Example 6, Comparative Examples 5-6

The starting materials described in the following Table 3 in the amounts described in Table 3 were mixed with heating at 80° C.-110° C. and applied to a silicone-treated PET film (release liner). PET cloth (support) was laminated on the surface of the obtained adhesive layer to give a laminated sheet. The laminated sheet was cut into a desired size to give the transdermal absorption preparations of Example 6 and Comparative Examples 5-6.

Examples 7-8

The starting materials described in the following Table 3 in the amounts described in Table 3 were used to produce a toluene solution, which was applied to a silicone-treated PET film (release liner) and dried with a hot-air dryer at 80° C. for 30 min. PET cloth (support) was laminated on the surface of the obtained adhesive layer to give a laminated sheet. The laminated sheet was cut into a desired size to give the transdermal absorption preparations of Examples 7-8.

TABLE 3

| reagents | Example 6 | Example 7 | Example 8 | Comparative Example 5 | Comparative Example 6 |
|---|---|---|---|---|---|
| elastomer: | | | | | |
| styrene-isoprene-styrene copolymer SIS5505 (manufactured by JSR) D1111 (manufactured by KRATON POLYMERS) | 30.0 | 30.0 | 30.0 | 15.0 | 15.0 |
| liquid paraffin (Kaydol: manufactured by Sonneborn) | | | | 79.0 | 80.7 |
| higher fatty acid ester: | | | | | |
| octyldodecyl myristate | 62.0 | 63.7 | 59.4 | | |
| crotamiton | 3.0 | 2.0 | 4.0 | 3.0 | 2.0 |
| lactic acid | | 1.0 | 2.0 | | 1.0 |
| dibutylhydroxytoluene | 2.0 | 2.0 | 2.0 | | |
| flurbiprofen | 3.0 | | | 3.0 | |
| diclofenac epolamine | | 1.3 | 2.6 | | 1.3 |
| total | 100.0 | 100.0 | 100.0 | 100.0 | 100.0 |

Experimental Example 3

Using the transdermal absorption preparations of Examples 6-8 and Comparative Examples 5-6, Yakuban Tape (Kaken Pharmaceutical Co., Ltd.) as a control product of Example 6 and Comparative Example 5, and Naboal Tape (Hisamitsu Pharmaceutical Co., Inc.) as a control product of Examples 7-8 and Comparative Example 6, the following in vitro transdermal permeation test was performed. An abdominal skin of male Wister rat (5-week-old) was set on a vertical Franz diffusion cell. Then, the transdermal absorption preparation was cut out in a circular shape with diameter 1.0 cm, the release liner was detached and the preparation was adhered to the rat skin on the diffusion cell (n=3). In the receptor side, using an ethanol-saline mixed solution (ethanol amount: 10%), the amount of donepezil that permeated through the rat skin after a given time was measured by high performance liquid chromatography (HPLC) under the following measurement conditions.

<HPLC Conditions>

HPLC system: high performance liquid chromatogram (LC2010C) manufactured by SHIMADZU CORPORATION column: ODS, 4.6 mmφ×15 cm, 5 μm column temperature: 40° C.

mobile phase: 0.1% aqueous sodium acetate solution/acetonitrile/SDS=7/3 (weight ratio)

detection wavelength: 254 nm flow: 0.7 mL/min

Figure 5:
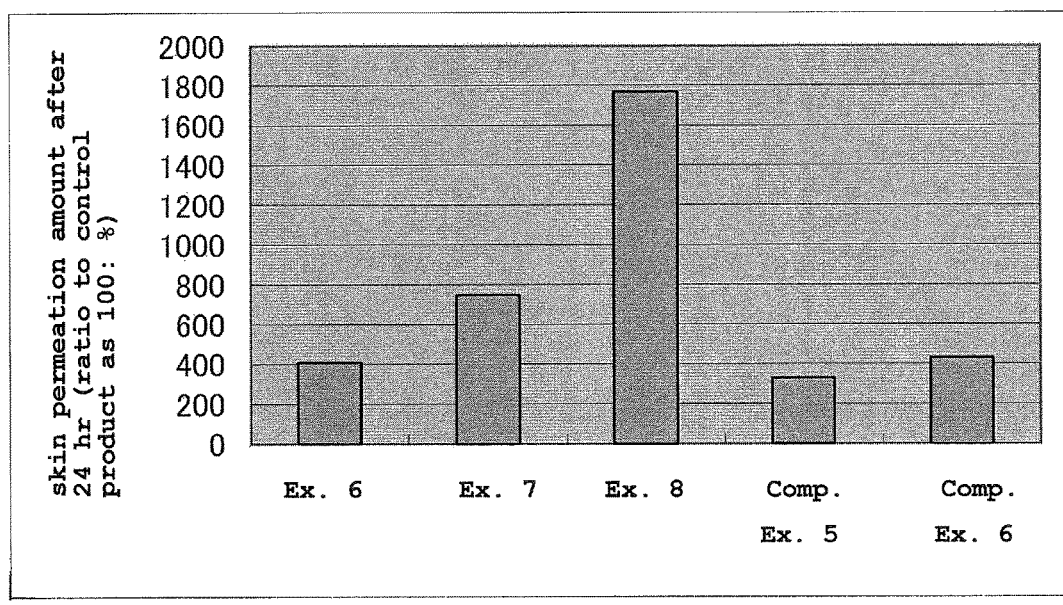
FIG. 5 is a graph showing transdermal permeation amount of flurbiprofen or diclofenac after 24 hr in in vitro transdermal permeation tests of Examples 6-8 and Comparative Examples 5-6.

The measurement results (permeation amount of flurbiprofen or diclofenac at 24 hr after adhesion: ratio to control product as 100) is shown in FIG. 5.

From FIG. 5, it is clear that the transdermal absorption transdermal absorption preparation of the present invention shows higher transdermal absorbability of drug than the commercially available control product. The transdermal absorption preparation of Example 6 shows higher transdermal permeation amount than the transdermal absorption preparation of Comparative Example 5, and the transdermal absorption preparations of Examples 7-8 show higher transdermal permeation amounts than the transdermal absorption preparation of Comparative Example 6. Therefrom it is clear that higher fatty acid ester is more advantageously used than liquid paraffin in these transdermal absorption preparations using drugs.

INDUSTRIAL APPLICABILITY

The transdermal absorption preparation of the present invention shows good transdermal absorbability of drugs, and is useful as a pharmaceutical product.

This application is based on a patent application No. 2015-257760 filed in Japan, the contents of which are incorporated in full herein.

The invention claimed is:

1. A transdermal absorption preparation comprising a support and a drug-containing adhesive layer formed on the support, wherein
the drug-containing adhesive layer comprises a thermoplastic elastomer and a higher fatty acid ester,
the thermoplastic elastomer is a styrene-isoprene-styrene block copolymer,
a content of the thermoplastic elastomer in the drug-containing adhesive layer is 24-44 wt % relative to the total amount of the drug-containing adhesive layer,
a solution viscosity of a 25 wt % toluene solution of the thermoplastic elastomer at 25° C. is not less than 0.5 Pa·s,
the higher fatty acid ester is an ester of a saturated fatty acid having a carbon number of 12-30 and a saturated or unsaturated aliphatic alcohol having a carbon number of 1-20,
a content of the higher fatty acid ester in the drug-containing adhesive layer is not less than 100 parts by weight and not more than 300 parts by weight per 100 parts by weight of the thermoplastic elastomer, and
a content of a tackifier in the drug-containing adhesive layer is not more than 10 wt % (0 wt % inclusive) relative to a total amount of the drug-containing adhesive layer.

2. The transdermal absorption preparation according to claim 1, wherein the drug-containing adhesive layer does not contain a tackifier.

3. The transdermal absorption preparation according to claim 1, wherein the drug-containing adhesive layer comprises polyisobutylene.

4. The transdermal absorption preparation according to claim 1, wherein the drug-containing adhesive layer comprises donepezil or a salt thereof as the drug.

5. The transdermal absorption preparation according to claim 4, wherein the drug-containing adhesive layer comprises higher fatty acid.

6. The transdermal absorption preparation according to claim 5, wherein the higher fatty acid has a carbon number of not less than 12 and not more than 30.

7. The transdermal absorption preparation according to claim 5, wherein the higher fatty acid comprises oleic acid.

8. The transdermal absorption preparation according to claim 3, wherein the polyisobutylene is (a) a mixture of polyisobutylene having a viscosity average molecular weight of 30,000-100,000 and polyisobutylene having a viscosity average molecular weight of 500,000-5,000,000 or (b) polyisobutylene having a viscosity average molecular weight of 100,000-500,000.

9. The transdermal absorption preparation according to claim 3, wherein the content of polyisobutylene in the drug-containing adhesive layer of the transdermal absorption preparation is not less than 0.1 part by weight and not more than 300 parts by weight per 100 parts by weight of the thermoplastic elastomer.

* * * * *